US00PP33530P2

(12) United States Plant Patent
Asaoka

(10) Patent No.: US PP33,530 P2
(45) Date of Patent: Sep. 28, 2021

(54) ***EPIPREMNUM AUREUM* PLANT NAMED 'GLOBAL GREEN'**

(50) Latin Name: *Epipremnum aureum*
Varietal Denomination: Global Green

(71) Applicant: Hiroaki Asaoka, Chigasaki (JP)

(72) Inventor: Hiroaki Asaoka, Chigasaki (JP)

( * ) Notice: Subject to any disclaimer, the term of this patent is extended or adjusted under 35 U.S.C. 154(b) by 0 days.

(21) Appl. No.: 16/602,442

(22) Filed: Oct. 4, 2019

(51) Int. Cl.
*A01H 5/00* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 5/00
See application file for complete search history.

*Primary Examiner* — Kent L Bell
(74) *Attorney, Agent, or Firm* — Adrienne C. Love

(57) ABSTRACT

A new and distinct *Epipremnum aureum* cultivar named 'Global Green' is disclosed, characterized by variegated leaves with two monochromatic colors and a fuller and wider typical plant with longer stems than its comparators. The new variety is an *Epipremnum aureum*, normally produced as an ornamental plant.

6 Drawing Sheets

Latin name of the genus and species of the plant claimed: *Epipremnum aureum.*

Varietal denomination: 'Global Green'.

CROSS-REFERENCES TO RELATED APPLICATIONS

None.

STATEMENT REGARDING FEDERALLY SPONSORED RESEARCH OR DEVELOPMENT

None.

BACKGROUND OF THE INVENTION

The present invention relates to a new and distinct cultivar of *Epipremnum*, botanically known as *Epipremnum aureum*, and hereinafter referred to by the name 'Global Green'.

The new *Epipremnum* plant cultivar was discovered by Hiroaki Asaoka in May 2016 in a plant nursery in Aichi, Japan. The instant plant was the result of a mutation that was naturally occurring. Asexual reproduction of the 'Global Green' by vegetative cuttings was first performed in September, 2016 in Aichi, Japan and has shown that the unique features of this cultivar are stable and reproduced true to type in successive generations of asexual reproduction.

SUMMARY OF THE INVENTION

The cultivar 'Global Green' has not been observed under all possible environmental conditions. The phenotype may vary somewhat with variations in environment such as temperature, day length, and light intensity without, however, any variance in genotype.

The following traits have been repeatedly observed and are determined to be the unique characteristics of 'Global Green'. These characteristics in combination distinguish 'Global Green' as a new and distinct *Epipremnum aureum* cultivar:

1. Centered green variegated leaves, with a more monochromatic appearance and more defined areas within which each of the two colors resides.
2. Patch of moderate yellow green color, of varying shape and size on either side of the midrib, on moderate olive-green background on a single leaf.
3. Mid-sized ovate/egg-shaped leaf with a pointy top.
4. Stems moderately strong with light yellow green and moderate yellow green colored appearance.

Plants of 'Global Green' can be compared to plants of the species selection, *Epipremnum aureum*. However, 'Global Green' differs from the plants of the mutation species selection in the following characteristics:

1. Plants of 'Global Green' produced variegated leaves that have two colors, where the primary color is moderate yellow green and the secondary color is moderate olive green.
2. Plants of 'Global Green' produced stems that were longer and slightly thicker.
3. Plants of 'Global Green' display ovate/egg shaped leaves with a pointy top.
4. Plants of 'Global Green' are wider and more dense.

BRIEF DESCRIPTION OF THE PHOTOGRAPHS

The accompanying colored photographs illustrate the overall appearance of the new *Epipremnum* showing the colors as true as it is reasonably possible to obtain in color reproductions of this type. Colors in the photograph may differ slightly from the color values cited in the detailed botanical description of the new variety which accurately describes the colors of the new *Epipremnum* plant.

DETAILED BOTANICAL DESCRIPTION OF THE NEW VARIETY

Figure 1:
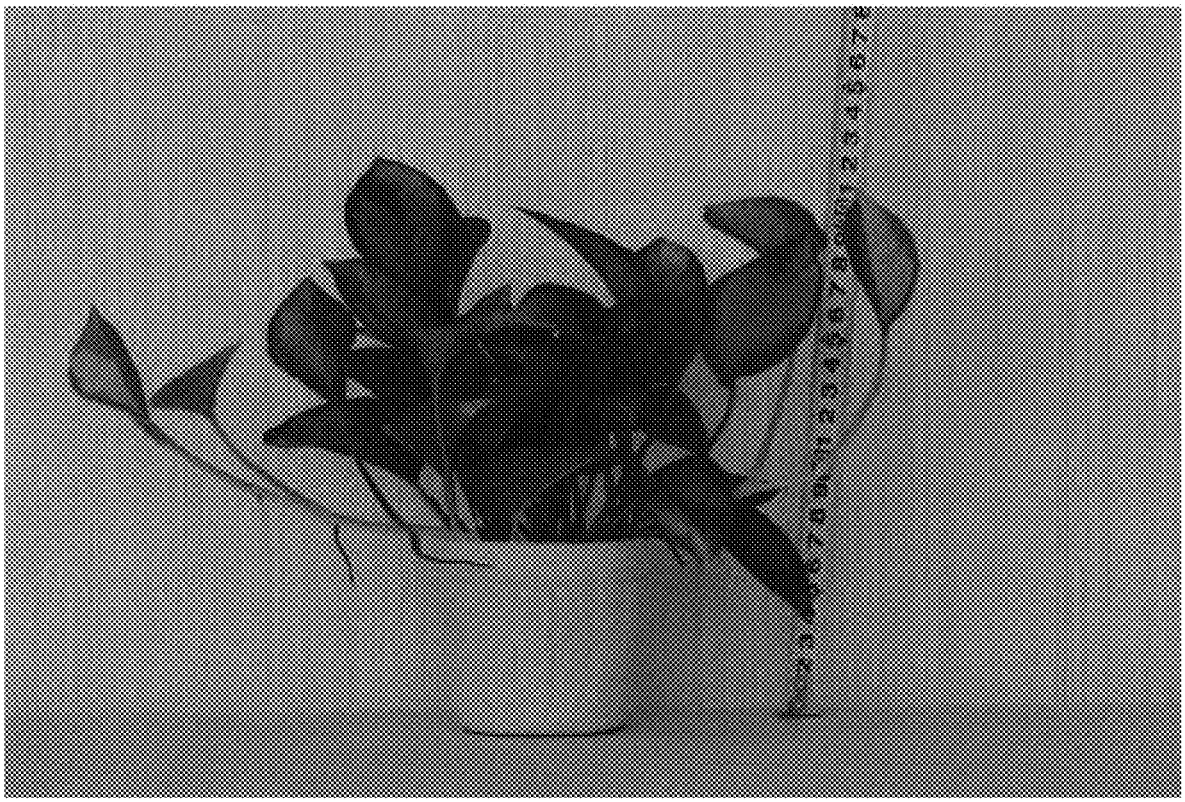
FIG. 1 is a perspective view of a typical plant of 'Global Green', grown in a 9 cm diameter container.
Figure 2:
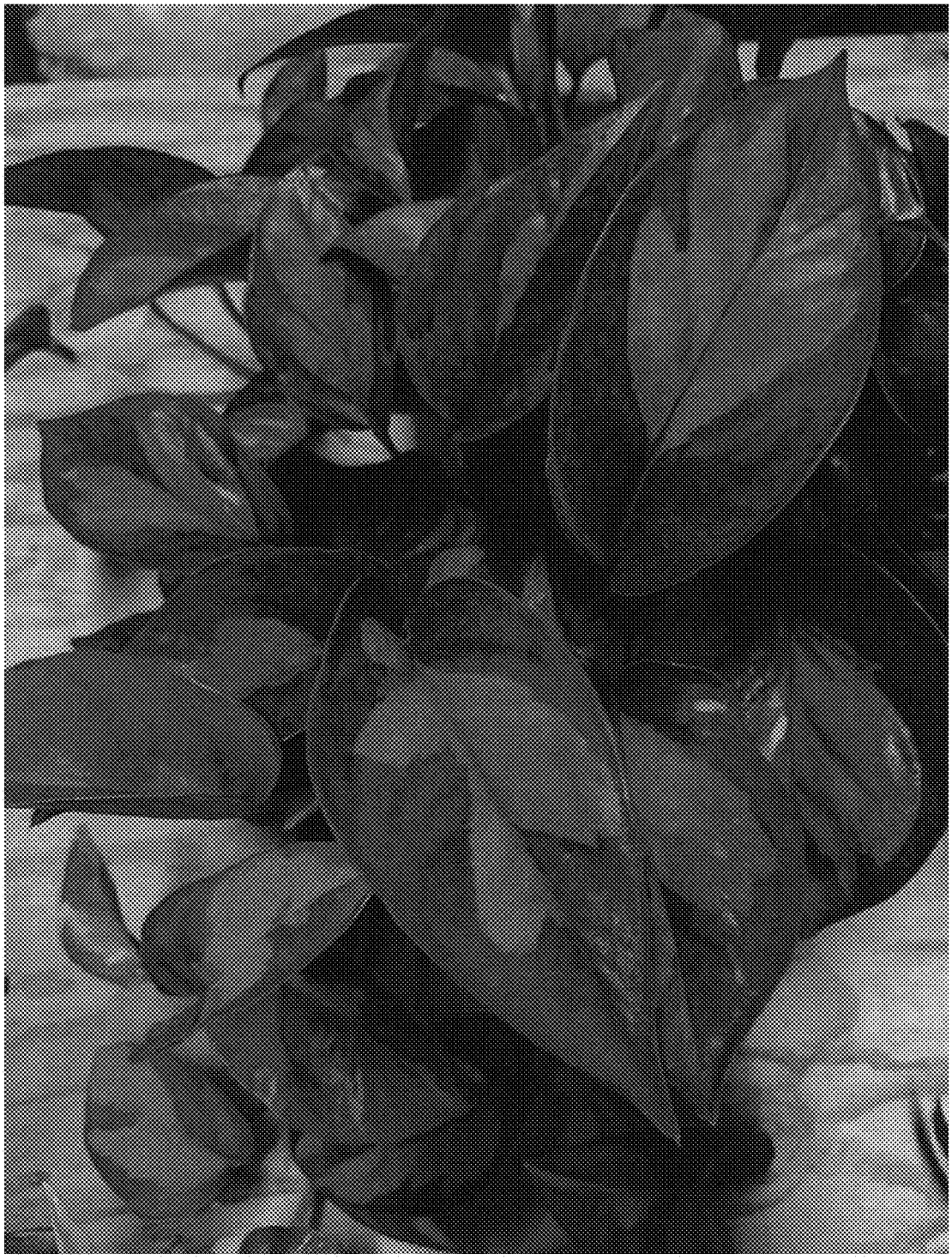
FIG. 2 is a close-up view of a typical foliar variegation of 'Global Green', illustrating the variegation of the leaves.
Figure 3:
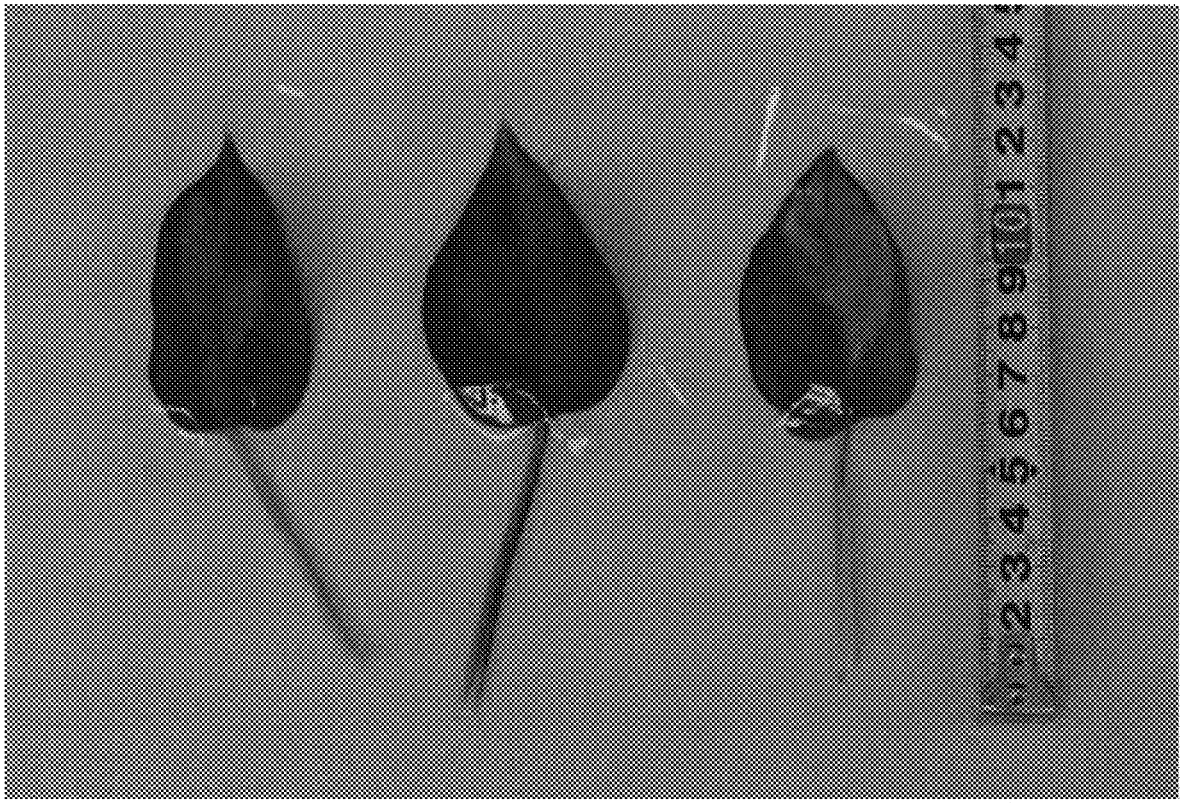
FIG. 3 is a close-up view of typical leaves and typical petiole of 'Global Green', illustration the variegation, length and width of the leaves and length and width of the petiole.
Figure 4:
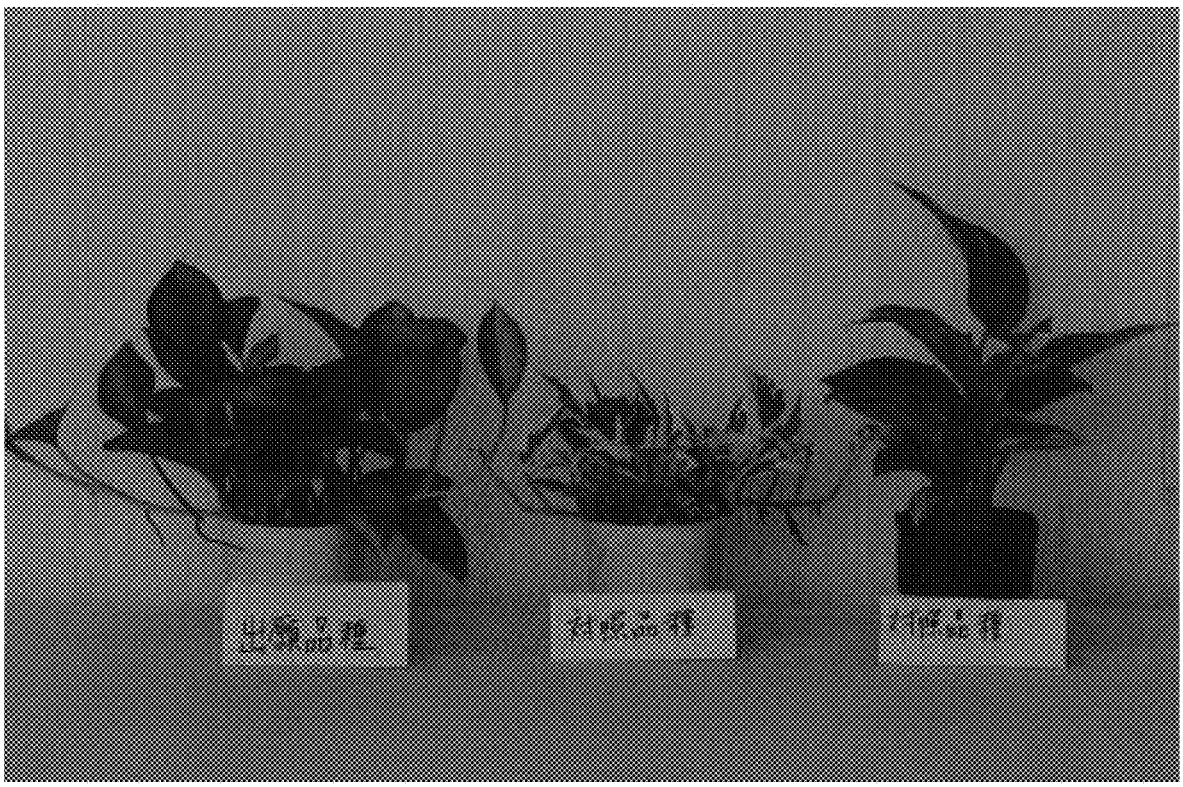
FIG. 4 is a perspective view of a typical plant of 'Global Green' on the far left, in comparison to mature plants of the unpatented plant varieties 'Asaoka First' (middle) and 'Golden Pothos' (right) illustrating the size and shape of the entire plants as grown in a greenhouse.
Figure 5:
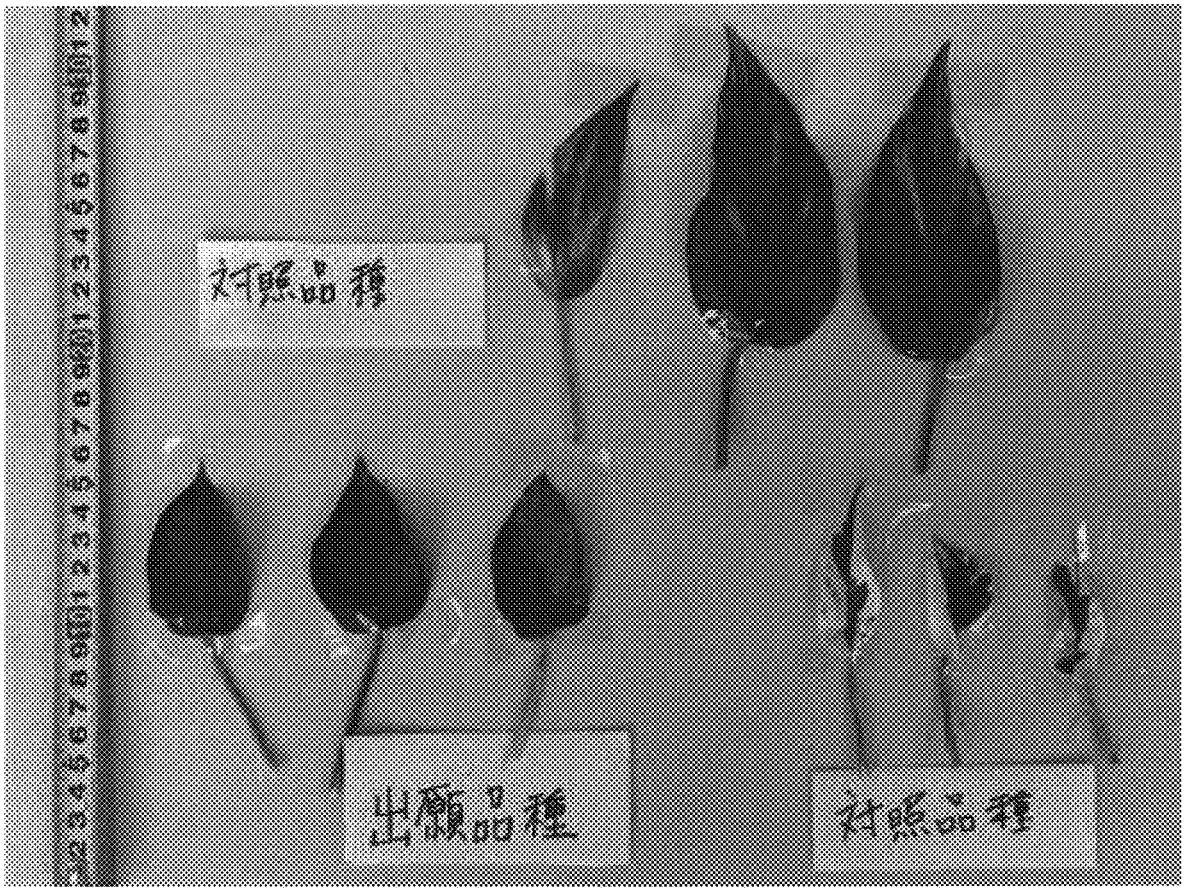
FIG. 5 is a perspective view of a typical leaf and typical petiole of 'Global Green' on the bottom left in comparison to typical leaves of the unpatented plant varieties 'Asaoka First' (bottom right) and 'Golden Pothos' (top), illustrating the size, shape and color of the leaves and length of petiole.
Figure 6:
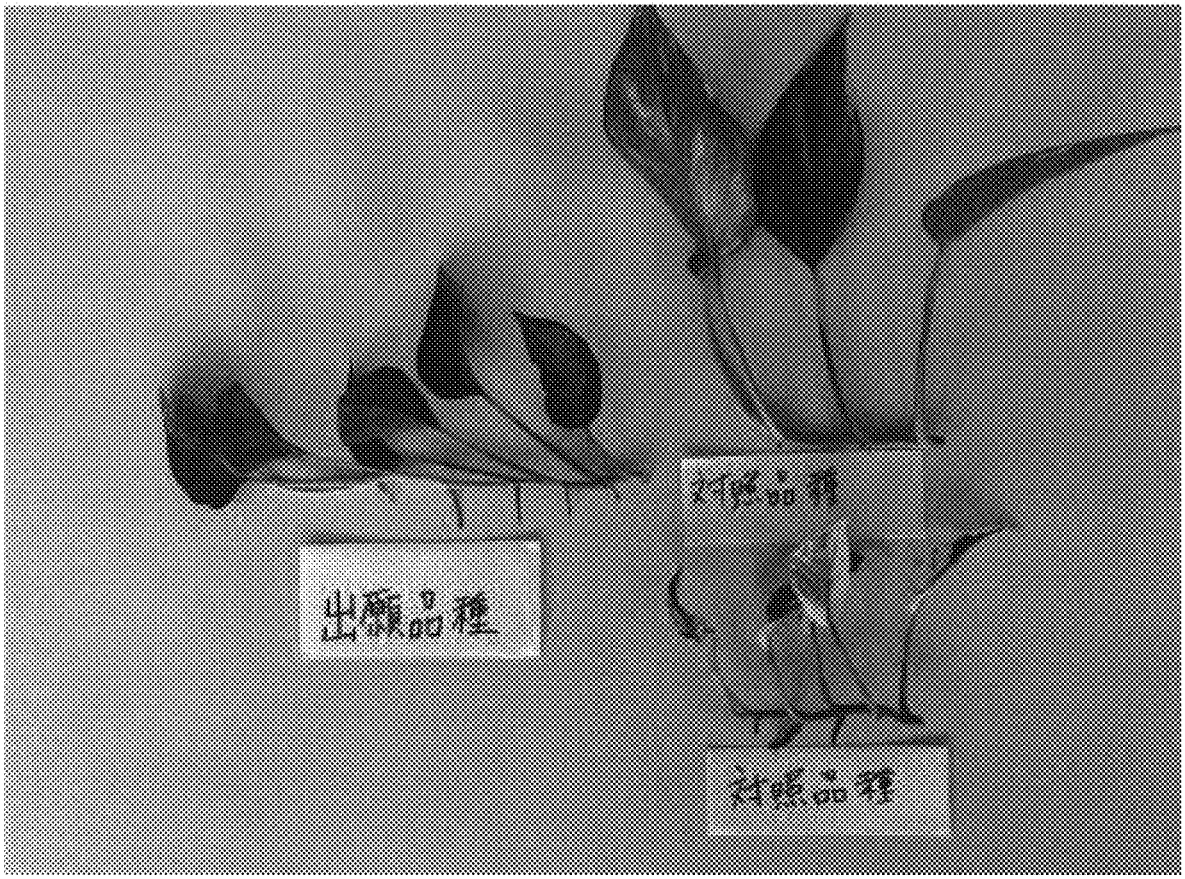
FIG. 6 is a perspective view of a typical stem and roots of 'Global Green' on the left in comparison to typical stems and roots of 'Asaoka First' (bottom right) and 'Golden Pothos' (top right), illustrating the size, shape and color of the stems and size and position of the roots.

The aforementioned photographs and the following observations, measurements, and values describes plants of the new *Epipremnum* grown in Aichi, Japan in conditions of 60% shading and 24 hr ventilation all year around in 9 cm containers and under cultural practices of commercial *Epipremnum* production. During the production of the plants, temperatures ranged from about 20 (winter)-40 (highest in summer) degrees Celsius and light levels were normal sunlight.

Plants were growing about 3.5 months when the photographs and the description were taken. However, it should be noted that the cultivar 'Global Green' can grow up to 30 cm tall, maybe taller given time, if grown in larger pots. Even at this height, the characteristics of the 'Global Green' as described remain true.

The following is a detailed description of the new plant characteristics with color in terminology in accordance with The Royal Horticultural Society Colour Chart, Edition V (2007), except where ordinary dictionary significance of color is indicated.

Botanical classification: *Epipremnum aureum*.

Common Name: 'Global Green'.

PROPAGATION

Type: By cuttings.

Time to initiate roots, summer: About 3 weeks at temperatures of 21 degrees to 35 degrees Celsius.

Time to initiate roots, winter: About 4 weeks at temperatures of 15 degrees to 29 degrees Celsius.

Time to produce a rooted young plant, spring: About 9 weeks at temperatures of 21 degrees to 35 degrees Celsius.

Root description: Thick and dense; fleshy when plants mature; typical of species.

PLANT

Growth habit: Low growing, trailing, cascading.

Plant shape: Plants are full, compact and have dense foliage.

Height (from soil level to top of leaf plane): Approximately 15 cm to top of highest leaf.

Plant diameter or spread: Approximately 20 cm to 30 cm.

Growth rate: Rapid.

Stem description:

*Length*.—About 13 cm.

*Diameter*.—About 3.8 mm.

*Internode length*.—About 2.4 cm.

*Texture*.—Smooth.

*Branching*.—Stems do not tend to branch.

*Colors, mature*.—Moderate yellow green 138B and light yellow green 138D.

Age of plant described: Approximately 3.5 months.

FOLIAGE

Leaves:

*Arrangement*.—Alternate.

*Average length*.—About 7.6 cm.

*Average width*.—About 4.5 cm.

*Shape of blade*.—Ovate, egg shape.

*Apex*.—Acuminate, pointy.

*Base*.—Truncate, flat.

*Attachment*.—Stalked.

*Margin*.—Entire.

*Texture of top and bottom surface*.—Smooth.

*Leaf internode length*.—Approximately 2.4 cm.

*Color*.—Mature leaves, upper surface: Centered variegation, areas of moderate yellow green 137C and moderate olive-green 137A; Mature leaves, lower surface: primary color moderate yellow green 137C and secondary color of moderate olive green 137A.

*Venation*.—Reticulate, with lower surface venation color moderate olive green 137A.

Petiole:

*Length*.—About 5 to 6 cm.

*Diameter*.—About 2 to 3 mm.

*Strength*.—Strong.

*Texture*.—Smooth.

*Color*.—Moderate yellow green 137C.

FLOWER

Blooming not observed on the new cultivar.

OTHER CHARACTERISTICS

Seed production: No seed production to date has been observed.

Disease resistance: Moderate tolerance to disease under normal conditions.

Insect resistance: Moderate tolerance to insects under normal conditions.

Temperature tolerance: Low temperature tolerance to at least 10 degrees Celsius, high temperatures to at most 45 degrees Celsius.

Other distinctive characteristics: Overall commercially interesting appearance. When compared to its closest comparison cultivars 'Asaoka First' and 'Golden Pathos', respectively, 'Global Green' differs in the following characteristics:

1. 'Global Green' has centered variegation that consists of two colors, rather than 3.
2. 'Global Green' has a primary color of moderate yellow green 137C that contrasts with its secondary color of moderate olive-green 137A less than its comparators.
3. 'Global Green' is fuller and wider as a whole than its comparators.

What is claimed is:

1. A new and distinct cultivar of *Epipremnum aureum* plant named 'Global Green' as illustrated and described.

* * * * *